(12) United States Patent
Roettger et al.

(10) Patent No.: US 7,541,506 B2
(45) Date of Patent: *Jun. 2, 2009

(54) METHOD FOR THE TELOMERISATION OF NON-CYCLIC OLEFINS

(75) Inventors: Dirk Roettger, Recklinghausen (DE); Ralf Jackstell, Cuxhaven (DE); Holger Klein, Rostock (DE); Matthias Beller, Nienhagen (DE)

(73) Assignee: OXENO Olefinchemie GmbH, Marl (DE)

( * ) Notice: Subject to any disclaimer, the term of this patent is extended or adjusted under 35 U.S.C. 154(b) by 531 days.

This patent is subject to a terminal disclaimer.

(21) Appl. No.: 10/517,620

(22) PCT Filed: Jun. 17, 2003

(86) PCT No.: PCT/EP03/06356

§ 371 (c)(1),
(2), (4) Date: Dec. 23, 2004

(87) PCT Pub. No.: WO2004/002931

PCT Pub. Date: Jan. 8, 2004

(65) Prior Publication Data

US 2005/0240039 A1    Oct. 27, 2005

(30) Foreign Application Priority Data

Jun. 29, 2002  (DE) ............... 102 29 290
Mar. 22, 2003  (DE) ............... 103 12 829

(51) Int. Cl.
*C07C 2/02*  (2006.01)
*C07C 209/00*  (2006.01)

(52) U.S. Cl. ............ 585/507; 585/506; 560/244; 560/265; 564/485; 564/690

(58) Field of Classification Search ............ 585/505, 585/506, 507; 560/244, 265; 564/485, 690
See application file for complete search history.

(56) References Cited

U.S. PATENT DOCUMENTS

| 6,627,782 | B2 | 9/2003 | Kaizik et al. |
| 7,026,523 | B2 * | 4/2006 | Rottger et al. ............ 585/638 |
| 2004/0059170 | A1 | 3/2004 | Rottger et al. |
| 2004/0242947 | A1 | 12/2004 | Beller et al. |
| 2005/0038273 | A1 | 2/2005 | Rottger et al. |
| 2005/0065387 | A1 | 3/2005 | Beller et al. |

FOREIGN PATENT DOCUMENTS

| WO | WO 92/10450 | * | 6/1992 |
| WO | 02/100803 | | 12/2002 |
| WO | WO 02/100803 | | 12/2002 |

OTHER PUBLICATIONS

U.S. Appl. No. 10/538,475, filed Jun. 7, 2005, Kaizik, et al.
U.S. Appl. No. 10/538,359, filed Jun. 13, 2005, Rottger, et al.
U.S. Appl. No. 10/562,454, filed Dec. 27, 2005, Krissmann, et al.
U.S. Appl. No. 11/574,060, filed Feb. 22, 2007, Borgmann, et al.
U.S. Appl. No. 11/574,018, filed Feb. 21, 2007, Borgmann, et al.
U.S. Appl. No. 11/574,063, filed Feb. 22, 2007, Nierlich, et al.
U.S. Appl. No. 10/593,330, filed Sep. 19, 2006, Borgmann, et al.
U.S. Appl. No. 11/721,978, filed Jun. 16, 2007, Beller, et al.
U.S. Appl. No. 12/088,041, filed Mar. 25, 2008, Weise, et al.
U.S. Appl. No. 12/159,957, filed Jul. 2, 2008, Baumgarten, et al.

* cited by examiner

*Primary Examiner*—In Suk Bullock
(74) *Attorney, Agent, or Firm*—Oblon, Spivak, McClelland, Maier & Neustadt, P.C.

(57) ABSTRACT

The invention relates to a process for the telomerization of acyclic olefins having at least two conjugated double bonds (I) or mixtures in which such olefins are present with nucleophiles (II) using a metal-carbene complex as catalyst.

7 Claims, No Drawings

METHOD FOR THE TELOMERISATION OF NON-CYCLIC OLEFINS

CROSS REFERENCES TO RELATED APPLICATIONS

This application is a national stage application of International Patent Application No. PCT/EP2003/006356, filed on Jun. 17, 2003, and claims priority to German Patent Application No. 102 29 290.6, filed on Jun. 29, 2002, and German Patent Application No. 103 12 829.8, filed on Mar. 22, 2003, all of which are incorporated herein by reference in their entireties.

The present invention relates to a process for the telomerization of acyclic olefins having at least two conjugated double bonds (I) with nucleophiles (II) using a metal-carbene complex as catalyst.

For the purposes of the present invention, telomerization is the reaction of olefins having conjugated double bonds (conjugated dienes) in the presence of a nucleophile (telogen). The main products obtained are compounds made up of two equivalents of the diene and one equivalent of the nucleophile.

The products of the telomerization reaction are of industrial importance as versatile precursors for solvents, plasticizers, fine chemicals and intermediates for active compounds. The octadienol, octadienyl ethers or octadienyl esters obtainable from butadiene are potential intermediates in processes for preparing corresponding alkenes.

The telomerization of dienes with nucleophiles is an industrially interesting method of adding value to inexpensive, industrially available dienes. Owing to their ready availability, the use of butadiene, isoprene or cracker fractions obtained from these dienes is of particular interest. However, to the present time, the telomerization of butadiene is being employed in practice only by Kuraray in the fine chemicals sector for the synthesis of 1-octanol. The reasons which prevent the wider use of telomerization processes include unsatisfactory catalyst activities, catalyst productivities and selectivity problems with telomerization catalysts. Thus, the known telomerization processes result in high catalyst costs and/or by-products which prevent industrial implementation.

Compounds which have been found to be effective catalysts for telomerization are, inter alia, halogen-free palladium (0) and palladium (II) compounds (A. Behr, in "*Aspects of Homogeneous Catalysis*"; editor R. Ugo, D. Reidel Publishing Company, Doordrecht/Boston/Lancaster, 1984, Vol. 5, 3). In addition, compounds of other transition metals such as cobalt (R. Baker, A. Onions, R. J. Popplestone, T. N. Smith, *J. Chem. Soc., Perkin Trans. II* 1975, 1133-1138), rhodium, nickel (R. Baker, D. E. Halliday, T. N. Smith, *J. Organomet. Chem.* 1972, 35, C61-C63; R. Baker, *Chem. Rev.* 1973, 73, 487-530; R. Baker, A. H. Cook, T. N Smith, *J. Chem. Soc., Perkin Trans. II* 1974, 1517-1524.) and platinum have also been used as catalysts.

The telomerization of dienes is described comprehensively in the technical literature. In the telomerization of butadiene with methanol, for example, the abovementioned catalysts generally give mixtures of the products 1a, 1b, 2, 3 (below) where X=O, $R^a$=Me. Main products are the desired, industrially important linear telomers 1a and 1b. However, significant proportions of the branched telomer 2 and of 1,3,7-octatriene 3 are formed.

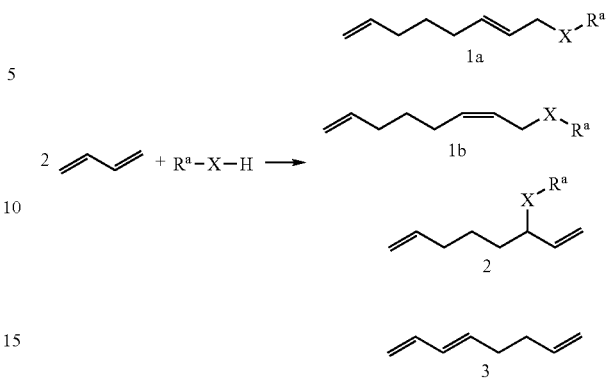

Furthermore, 4-vinyl-1-cyclohexene (Diels-Alder product of butadiene) is formed in variable yields together with, generally in only small amounts, further by-products. This range of products is generally also found when using other nucleophiles having active hydrogen atoms, in which case the corresponding radicals of the respective nucleophile are introduced in place of the methoxy group.

The significant formation of the abovementioned by-products is a further factor which makes implementation of an economical and environmentally friendly process extraordinarily difficult. Although telomerization of butadiene with methanol has been intensively studied and patented by a number of companies, the abovementioned problems have not been solved satisfactorily.

In a continuous process described by Dow Chemical in WO 91/09822 in 1989, in which palladium acetylacetonate/triphenylphosphine is used as catalyst, catalyst productivities (turnover numbers) up to 44,000 were achieved. However, the chemoselectivities to the target product 1 at such catalyst turnover numbers are <85%.

National Distillers and Chem. Corp. (U.S. Pat. No. 4,642, 392, U.S. Pat. No. 4,831,183) described a batch process for the preparation of octadienyl ethers in 1987. Here, the product mixture was separated off from the catalyst (palladium acetate/5 eq. of triphenylphosphine) by distillation, leaving the catalyst as a solution in tetraglyme. The catalyst can be reused up to twelve times, with further phosphine being added each time. However, the first batch gave the linear ether in a yield of only 57% (corresponds to a TON of 2000). The n/iso ratio of product 1 to product 2 is in this case only 3.75:1. In a further patent of National Distillers, the product mixture was separated from the reaction solution by extraction with hexane. The telomerization was carried out in dimethylformamide or sulfolane using the catalyst mixture palladium(II) acetate/3 eq. of triphenylphosphinemonosulfonate. The first batch gave the linear telomer with a TON of 900. The selectivity to the linear alcohol was a low 40%.

Longer-chain primary alcohols such as ethanol, propanol and butanol (J. Beger, H. Reichel, *J. Prakt. Chem.* 1973, 315, 1067) form the corresponding telomers with butadiene. However, the catalyst activity of the known catalysts is in this case even lower than in the abovementioned cases. Thus, under identical reaction conditions [Pd(acetylacetonate)$_2$/PPh$_3$/butadiene/alcohol=1:2:2000:5000; 60° C./10 h], the telomers of methanol are formed in a yield of 88%, those of propanol are formed in a yield of 65% and those of nonanol are formed in a yield of only 21%.

In summary, it can be said that the known palladium-phosphine catalysts for the telomerization reactions of butadiene with alcohols do not allow satisfactory selectivities of >95% chemoselectivity and regioselectivity, as required for an ecologically advantageous process, to be achieved.

Like alcohols, carboxylic acids are suitable nucleophiles in telomerization reactions. Acetic acid and butadiene give good yields of the corresponding octadienyl derivatives 1a, 1b and 2 with $R^a$=Me—CO, X=O (DE 2 137 291). The ratio of products 1/2 can be influenced via the ligands of the palladium (D. Rose, H. Lepper, *J. Organomet. Chem.* 1973, 49, 473). A ratio of 4/1 could be achieved using triphenylphosphine as ligand, and the ratio could be increased to 17/1 when tris(o-methylphenyl)phosphite was used. Other carboxylic acids such as pivalic acid, benzoic acid or methacrylic acid and also dicarboxylic acids can likewise be reacted with butadiene.

Shell Oil has described a process based on the telomerization of conjugated dienes with carboxylic acids for the preparation of α-olefins in U.S. Pat. No. 5,030,792.

Telomerization reactions in which water is used as nucleophile have been studied intensively by, inter alia, Kuraray (U.S. Pat. No. 4,334,117, U.S. Pat. No. 4,356,333, U.S. Pat. No. 5,057,631). Here, phosphines, usually water-soluble phosphines, or phosphonium salts (EP 0 296 550) are usually used as ligands. The use of water-soluble diphosphines as ligands is described in WO 98/08 794, and DE 195 23 335 discloses the reaction of alkadienes with water in the presence of phosphonite or phosphinite ligands.

The telomerization of butadiene with nucleophiles such as formaldehyde, aldehydes, ketones, carbon dioxide, sulfur dioxide, sulfinic acids, β-keto esters, β-diketones, malonic esters, α-formyl ketones and silanes has likewise been described.

Most of the work on telomerization has been carried out using butadiene. However, this reaction can also be applied to other dienes having conjugated double bonds. These can formally be regarded as derivatives of butadiene in which hydrogen atoms have been replaced by other groups. Isoprene is of particular industrial importance. Since, in contrast to butadiene, isoprene is an unsymmetrical molecule, telomerization results in formation of further isomers (J. Beger, Ch. Duschek, H. Reichel, *J. Prakt. Chem.* 1973, 315, 1077-89). The ratio of these isomers is influenced considerably by the type of nucleophile and the choice of ligands.

Owing to the abovementioned importance of the telomerization products and the problems associated with the present state of the art, there is a great need for new catalyst systems for telomerization reactions which make it possible to carry out the reactions on an industrial scale with high catalyst productivity and give telomerization products in high yield and purity.

It has surprisingly been found that the telomerization reactions of an acyclic olefin with a nucleophile are catalyzed by metals of groups 8 to 10 of the Periodic Table and particular carbene ligands so as to give high conversions and selectivities.

The invention accordingly provides a process for the catalytic telomerization of acyclic olefins having at least two conjugated double bonds, in particular acyclic olefins of the formula (I)

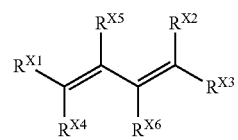

(I)

with at least one nucleophile, wherein complexes comprising metals of groups 8 to 10 of the Periodic Table of the Elements and at least one carbene ligand having one of the formulae

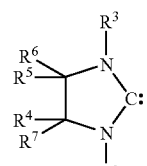

(III)

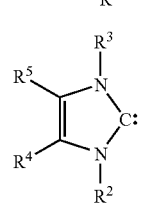

(IV)

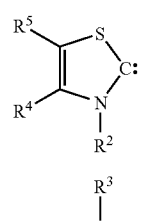

(V)

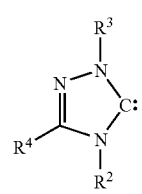

(VI)

where
$R^{X1}$, $R^{X2}$, $R^{X3}$, $R^{X4}$, $R^{X5}$, $R^{X6}$ are identical or different and are each H or a linear, branched, substituted or unsubstituted cyclic or alicyclic aliphatic or aromatic group having from 1 to 24 carbon atoms, $R^2$; $R^3$: are identical or different and are each a) a linear, branched, substituted or unsubstituted cyclic or alicyclic alkyl group having from 1 to 24 carbon atoms,
 or b) a substituted or unsubstituted, monocyclic or polycyclic aryl group having from 6 to 24 carbon atoms
 or c) a monocyclic or polycyclic, substituted or unsubstituted heterocycle having from 4 to 24 carbon atoms and at least one heteroatom from the group consisting of N, O, S, $R^4$, $R^5$, $R^6$, $R^7$: are identical or different and are each hydrogen, alkyl, aryl, heteroaryl, —CN, —COOH, —COO-alkyl, —COO-aryl, —OCO-alkyl, —OCO-aryl, —OCOO-alkyl, —OCOO-aryl, —CHO, —CO-alkyl, —CO-aryl, —O-alkyl, —O-aryl, —NH$_2$, —NH(alkyl), —N(alkyl)$_2$, —NH(aryl), —N(aryl)$_2$, —F, —Cl, —Br, —I, —OH, —CF$_3$, —NO$_2$, -ferrocenyl, —SO$_3$H, —PO$_3$H$_2$, where the alkyl groups have 1-24 carbon atoms and the aryl groups have from 5 to 24 carbon atoms and the radicals R$^4$ and R$^5$ may also be part of a bridging aliphatic or aromatic ring, with the proviso that when the metal of groups 8 to 10 of the Periodic Table is Pd, R$^2$ and/or R$^3$ have the meaning c), are used as catalyst.

R$^2$ and R$^3$ are in particular a monocyclic or polycyclic ring which contains at least one heteroatom selected from among the elements nitrogen, oxygen and sulfur and may bear further substituents selected from among the groups —CN, —COOH, COO-alkyl, —COO-aryl, —OCO-alkyl, —OCO-aryl, —OCOO-alkyl, —OCOO-aryl, —CHO, —CO-alkyl, —CO-aryl, -aryl, -alkyl, —O-alkyl, —O-aryl, —NH$_2$, —NH(alkyl), —N(alkyl)$_2$, —NH(aryl), —N(aryl)$_2$, —F, —Cl, —Br, —I, —OH, —CF$_3$, —NO$_2$, -ferrocenyl, —SO$_3$H, —PO$_3$H$_2$. The alkyl groups have from 1 to 24 carbon atoms and the aryl groups have from 5 to 24 carbon atoms. When Pd is used as metal of groups 8 to 10 of the Periodic Table, one or both of the ligands R$^2$ and R$^3$ have these meanings.

The radicals R$^2$, R$^3$, R$^4$, R$^5$, R$^6$ and/or R$^7$ can be identical or different and may bear at least one substituent from the group consisting of —H, —CN, —COOH, —COO-alkyl, —COO-aryl, —OCO-alkyl, —OCO-aryl, —OCOO-alkyl, —OCOO-aryl, —CHO, —CO-alkyl, —CO-aryl, -aryl, -alkyl, -alkenyl, -allyl, —O-alkyl, —O-aryl, —NH$_2$, —NH(alkyl), —N(alkyl)$_2$, —NH(aryl), —N(aryl)$_2$, —F, —Cl, —Br, —I, —OH, —CF$_3$, —NO$_2$, -ferrocenyl, —SO$_3$H, —PO$_3$H$_2$, where the alkyl groups have from 1 to 24, preferably from 1 to 20, carbon atoms, the alkenyl groups have from 2 to 24 carbon atoms, the allyl groups have from 3 to 24 carbon atoms and the monocyclic or polycyclic aryl groups have from 5 to 24 carbon atoms.

The radicals R$^4$ to R$^6$ may also be covalently bound to one another, e.g. via CH$_2$ or CH groups.

Substituents having acidic hydrogen atoms can also have metal or ammonium ions in place of the protons.

The radicals R$^2$ and R$^3$ may be, inter alia, monocyclic or polycyclic rings containing at least one heteroatom. These are, for example, radicals which are derived from five- and six-membered heteroalkanes, heteroalkenes and heteroaromatics such as 1,4-dioxane, morpholine, γ-pyran, pyridine, pyrimidine, pyrazine, pyrrole, furan, thiophene, pyrazole, imidazole, thiazole and oxazole. Specific examples of such radicals R2 and R3 are shown in the table below. In the table below. In the table, ~ in each case indicates the point of linkage to the five-membered heterocycle.

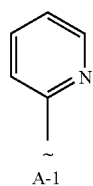

A-1

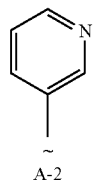

A-2

-continued

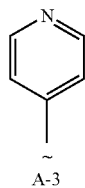

A-3

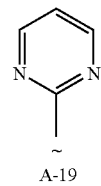

A-19

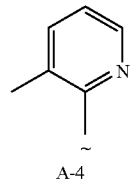

A-4

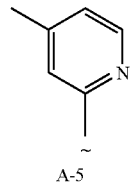

A-5

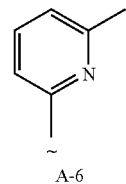

A-6

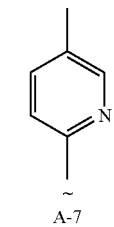

A-7

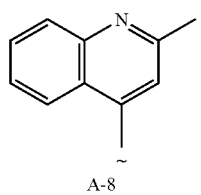

A-8

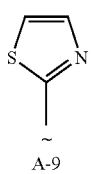

A-9

-continued

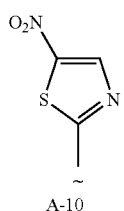
A-10

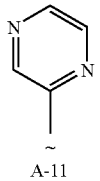
A-11

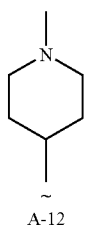
A-12

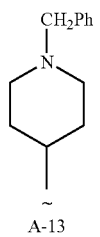
A-13

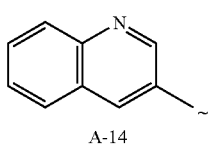
A-14

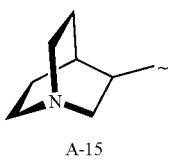
A-15

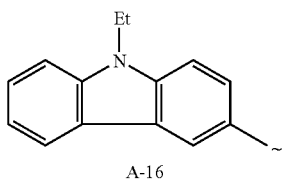
A-16

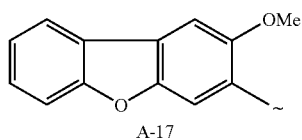
A-17

-continued

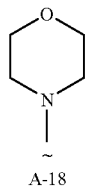
A-18

For the purposes of the present invention, carbene ligands include both free carbenes which can function as ligand and also carbenes coordinated to metals.

Suitable metals can be, for example, Pd, Fe, Ru, Os, Co, Rh, Ir, Ni or Pt.

In the telomerization carried out by the process of the invention, it is in principle possible to use all acyclic olefins having at least two conjugated double bonds. For the purposes of the present invention, the use of compounds of the formula (I), in particular 1,3-butadiene and isoprene (2-methyl-1,3-butadiene), is preferred. It is possible to use both the pure dienes and mixtures in which these dienes are present.

As mixtures comprising 1,3-butadiene/isoprene, preference is given to using mixtures of 1,3-butadiene or isoprene with other $C_3$-, $C_4$- and/or $C_5$-hydrocarbons. Such mixtures are obtained, for example, in cracking processes for the production of ethene, in which refinery gases, naphtha, gas oil, LPG (liquefied petroleum gas), NGL (natural gas liquid), etc, are reacted. The $C_4$ fractions obtained as by-product in these processes comprise, depending on the cracking process, variable amounts of 1,3-butadiene. Typical 1,3-butadiene concentrations in the $C_4$ fraction obtained from a naphtha steam cracker are from 20 to 70% of 1,3-butadiene.

The $C_4$ components n-butane, i-butane, 1-butene, cis-2-butene, trans-2-butene and i-butene, which are likewise present in these fractions, interfere only inconsequentially, if at all, in the reaction in the telomerization step.

Dienes having cumulated double bonds (1,2-butadiene, allene, etc) and alkynes, in particular vinylacetylene can, on the other hand, act as moderators in the telomerization reaction. It is therefore advantageous to remove the alkynes and possibly the 1,2-butadiene beforehand (e.g. as described in DE 195 23 335). This can, if possible, be carried out by means of physical processes such as distillation or extraction. Possible chemical routes are selective hydrogenation of the alkynes to alkenes or alkanes and reduction of the cumulated dienes to monoenes. Methods of carrying out such hydrogenations are prior art and are described, for example, in WO 98/12160, EP-A-0 273 900, DE-A-37 44 086 or U.S. Pat. No. 4,704,492.

As nucleophiles in the process of the invention, preference is given to using compounds of the formula (II)

$$R^1\text{-}Z\text{-}R^{1'} \quad (II)$$

where

Z is O, $N(R^{1''})$, $N(CH_2CH=CH_2)$, $C(H_2)$, $Si(R^{1'''})(OH)$, $C=O$, $C(H)(NO_2)$ or $S(O_2)$, viz.

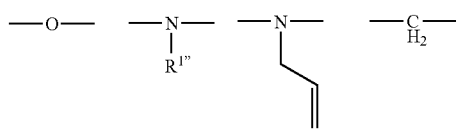

-continued

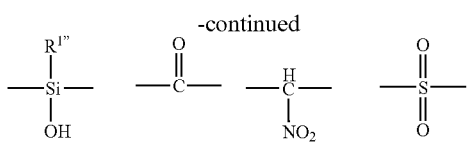

and $R^1$, $R^{1'}$ or $R^{1''}$ are identical or different and are each H, a substituted or unsubstituted, linear, branched or cyclic alkyl or alkenyl group having from 1 to 22 carbon atoms, a carboxyl group or an aryl group, where the radicals $R^1$, $R^{1'}$ may be joined to one another via covalent bonds and $R^1$ and $R^{1'}$ may bear identical or different substituents, e.g. one or more substituents selected from the group consisting of —CN, —COOH, —COO-alkyl, —CO-alkyl, -aryl, -alkyl, —COO-aryl, —CO-aryl, —O-alkyl, —O—CO-alkyl, —N-alkyl$_2$, —CHO, —SO$_3$H, —NH$_2$, —F, —Cl, —OH, —CF$_3$, —NO$_2$. The alkyl groups on the substituents preferably have from 1 to 24 carbon atoms and the aryl groups on the substituents preferably have from 5 to 24 carbon atoms.

In a preferred embodiment, compounds of the formula (IIa) or (IIb)

 (IIa)

 (IIb)

where $R^1$, $R^{1'}$ are identical or different and are each H, a substituted or unsubstituted, linear, branched or cyclic alkyl or alkenyl group having from 1 to 22 carbon atoms, a carboxyl group or an aryl group and the radicals $R^1$, $R^{1'}$ may be joined to one another via covalent bonds, are used as nucleophile (II).

$R^1$ and $R^{1'}$ may bear identical or different substituents, e.g. one or more substituents selected from the group consisting of —CN, —COOH, —COO-alkyl, —CO-alkyl, -aryl, -alkyl, —COO-Aryl, —CO-aryl, —O-alkyl, —O—CO-alkyl, —N-alkyl$_2$, —CHO, —SO$_3$H, —NH$_2$, —F, —Cl, —OH, —CF$_3$, —NO$_2$. The alkyl groups have from 1 to 24 carbon atoms and the aryl groups have from 5 to 24 carbon atoms.

As nucleophiles, preference is given to using any compounds having the formula (II). Examples of telogens of the formula (II) are water,
alcohols and phenols such as methanol, ethanol, n-propanol, isopropanol, allyl alcohol, butanol, octanol, 2-ethylhexanol, isononanol, benzyl alcohol, cyclohexanol, cyclopentanol, 2-methoxyethanol, phenol or 2,7-octadien-1-ol,
dialcohols such as ethylene glycol, 1,2-propanediol, 1,3-propanediol, 1,4-butanediol, 1,2-butanediol, 2,3-butanediol and 1,3-butanediol,
polyols such as glycerol, glucose, sucrose,
hydroxy compounds such as α-hydroxyacetic esters,
carboxylic acids such as acetic acid, propanoic acid, butanoic acid, isobutanoic acid, benzoic acid, 1,2-benzenedicarboxylic acid, 1,3-benzenedicarboxylic acid, 1,4-benzene-dicarboxylic acid, 1,2,4-benzenetricarboxylic acid,
ammonia,
primary amines such as methylamine, ethylamine, propylamine, butylamine, octylamine, 2,7-octadienylamine, dodecylamine, aniline, ethylenediamine or hexamethylenediamine,
secondary amines such as dimethylamine, diethylamine, N-methylaniline, bis(2,7-octadienyl)amine, dicyclohexylamine, methylcyclohexylamine, pyrrolidine, piperidine, morpholine, piperazine or hexamethylenimine.

Telogens which can themselves be obtained by a telomerization reaction can be used directly or else be formed in situ. Thus, for example, 2,7-octadien-1-ol can be formed in situ from water and butadiene in the presence of the telomerization catalyst, 2,7-octadienylamine can be obtained from ammonia and 1,3-butadiene, etc.

Particularly preferred telogens are water, methanol, ethanol, n-butanol, allyl alcohol, 2-methoxyethanol, phenol, ethylene glycol, 1,3-propanediol, glycerol, glucose, sucrose, acetic acid, butanoic acid, 1,2-benzenedicarboxylic acid, ammonia, dimethylamine and diethylamine.

The process of the invention is preferably carried out in the presence of a solvent.

As solvent, use is generally made of the nucleophile employed, if it is present as a liquid under the reaction conditions. However, it is also possible to use other solvents. The solvents used should be largely inert. Preference is given to the addition of solvents when using nucleophiles which are present as solids under the reaction conditions or in the case of products which would be obtained as solids under the reaction conditions. Suitable solvents include, inter alia, aliphatic, cycloaliphatic and aromatic hydrocarbons such as $C_3$-$C_{20}$-alkanes, mixtures of lower alkanes ($C_3$-$C_{20}$), cyclohexane, cyclooctane, ethylcyclohexane, alkenes and polyenes, vinylcyclohexene, 1,3,7-octatriene, the $C_4$-hydrocarbons from $C_4$ fractions from crackers, benzene, toluene and xylene; polar solvents such as tertiary and secondary alcohols, amides such as acetamide, dimethylacetamide and dimethylformamide, nitriles such as acetonitrile and benzonitrile, ketones such as acetone, methyl isobutyl ketone and diethyl ketone; carboxylic esters such as ethyl acetate, ethers such as dipropyl ether, diethyl ether, dimethyl ether, methyl octyl ether, 3-methoxyoctane, dioxane, tetrahydrofuran, anisole, alkyl and aryl ethers of ethylene glycol, diethylene glycol and polyethylene glycol and other polar solvents such as sulfolane, dimethyl sulfoxide, ethylene carbonate, propylene carbonate and water. Ionic liquids, for example imidazolium or pyridinium salts, can also be used as solvents.

The solvents are used either alone or as mixtures of various solvents or nucleophiles.

The temperature at which the telomerization reaction is carried out is in the range from 10 to 180° C., preferably from 30 to 120° C., particularly preferably from 40 to 100° C. The reaction pressure is from 1 to 300 bar, preferably from 1 to 120 bar, particularly preferably from 1 to 64 bar and very particularly preferably from 1 to 20 bar.

In the process of the invention, it is essential that the telomerization reaction is carried out using catalysts based on metal complexes having carbene ligands of the formulae (III) to (VI).

Examples of carbene ligands corresponding to the formulae (III) to (VI) and complexes in which such ligands are present have been described in the technical literature (W. A. Herrmann, C. Köcher, *Angew. Chem.* 1997, 109, 2257; *Angew. Chem. Int. Ed. Engl.* 1997, 36, 2162; W. A. Herrmann, T. Weskamp, V. P. W. Böhm, *Advances in Organometallic Chemistry*, 2001, Vol. 48, 1-69; D. Bourissou, O. Guerret, F. P. Gabbai, G. Bertrand, *Chem. Rev.* 2000, 100, 39-91).

However, only few examples of carbene ligands and complexes bearing heterocyclic substituents are known (J. C. C. Chen, I. J. B. Lin, *Organometallics* 2000, 19, 5113).

The catalyst metal of groups 8 to 10 of the Periodic Table can be introduced into the process in various ways:
a) as metal-carbene complexes,
b) in the form of precursors from which the catalysts are formed in situ.

Option a)

Metal-carbene complexes have been described in the technical literature (cf. W. A. Herrmann, C. Köcher, Angew. Chem. 1997, 109, 2257; Angew. Chem. Int. Ed. Engl. 1997, 36, 2162; W. A. Herrmann, T. Weskamp, V. P. W. Böhm, Advances in Organometallic Chemistry, 2001, Vol. 48, 1-69; D. Bourissou, O. Guerret, F. P. Gabbai, G. Bertrand, Chem. Rev. 2000, 100, 39-91; J. C. C. Chen, I. J. B. Lin, Organometallics 2000, 19, 5113) and are obtainable by various routes. For example, the complexes can be formed by addition of carbene ligand onto metal compounds. This can be achieved with expansion of the ligand sphere or by breaking up of bridge structures. Metal compounds of the formula I can often be obtained from simple compounds of metals of groups 8 to 10 of the Periodic Table, e.g. salts or metal complexes (acetates, acetylacetonates, carbonyls, etc) by reaction with the carbene ligands. A further possibility is the replacement of ligands coordinated to the central metal by the carbene ligands. In this case, less strongly coordinating ligands (e.g. solvent molecules) are displaced by the carbene ligands.

For the purposes of the present invention, preference is given to using metal-carbene complexes having the formula

where
M is a metal of groups 8 to 10 of the Periodic Table of the Elements, X is a charged or uncharged, monodentate or polydentate ligands bound to the metal atom and
A is a singly charged anion or the chemical equivalent of a multiply charged anion, L is one or more ligands of the formulae III to VI, b is an integer from 1 to 3, a is an integer from 1 to 4×b, c=0 or an integer from 1 to 4×b and n=0 or an integer from 1 to 6.

The group A is preferably a halide, sulfate, phosphate, nitrate, pseudohalide, tetraphenylborate, tetrafluoroborate, hexafluorophosphate or carboxylate ion, among the latter preferably the acetate ion, or else a metal complex anion, for example tetrachloropalladate, tetrachloro-aluminate, tetrachloroferrate(II), hexafluoroferrate(III), tetracarbonylcobaltate.

The monodentate or polydentate ligands which may be present in the complexes of Fe, Ru, Co, Rh, Ir, Ni, Pd and Pt in addition to the carbene ligands are shown in the formula (VII) as X. X is hydrogen or the hydrogen ion, a halogen or halogen ion, pseudohalide, carboxylate ion, sulfonate ion, amide group, alkoxide group, acetylacetonate group, carbon monoxide, alkyl radical having from 1 to 7 carbon atoms, aryl radical having from 6 to 24 carbon atoms, isonitrile, nitrogen ligand, (for example nitrogen monoxide, nitrile, amine, pyridine), monoolefin, diolefin, alkyne, allyl group, -cyclopentadienyl group, π-aromatic or phosphorus ligand which coordinates via the phosphorous atom. Phosphorus ligands are preferably compounds of trivalent phosphorus, e.g. phosphines, phosphites, phosphonites, phosphinites. If a plurality of ligands X are present in the metal complex, they can be identical or different.

If the substituents of the carbene ligands of the formulae (III) to (VI) bear functional groups, these can likewise coordinate to the metal atom (chelating coordination, also described as hemilabile coordination in the literature (J. C. C. Chen, I. J. B. Lin, Organometallics 2000, 19, 5113).

Option b)

The metal carbene complexes are formed in situ from precursors and carbene ligand or a carbene ligand precursor.

As precursors of the metal complexes of groups 8 to 10 of the Periodic Table, it is possible to use, for example, salts or simple complexes of the metals, for example metal halides, metal acetates, metal acetylacetonates, metal carbonyls.

For the purposes of illustration, some specific examples of palladium compounds are palladium(II) acetate, palladium (II) chloride, palladium(II) bromide, lithium tetrachloro-palladate, palladium(II) acetylacetonate, palladium(0)-dibenzylideneacetone complexes, palladium(II) propionate, bis (acetonitrile)palladium(II) chloride, bis (triphenylphosphine)-palladium(II) dichloride, bis (benzonitrile)palladium(II) chloride, bis(tri-o-tolylphosphine)-palladium(0). Analogous compounds of the other metals of groups 8 to 10 of the Periodic Table can likewise be used.

The carbenes of the formulae (III) to (VI) are used in the form of free carbenes or as metal complexes or are generated in situ from carbene precursors.

Suitable carbene precursors are, for example, salts of the carbenes having the formulae (VIII) to (XI),

where $R^2$, $R^3$, $R^4$, $R^5$, $R^6$, $R^7$ are as defined above and Y is a singly charged anionic group or, corresponding to the stoichiometry, part of a multiply charged anionic group.

Examples of Y are halides, hydrogensulfate, sulfate, phosphate, alkoxide, phenoxide, alkylsulfates, arylsulfates, borates, hydrogen carbonate, carbonate, alkylcarboxylates, arylcarbonates.

The carbenes can be liberated from the corresponding salts of the carbenes, if appropriate by reaction with an additional base. Suitable bases are, for example, metal hydrides, metal alkoxides, carbonylmetalates, metal carboxylates, metal amides or metal hydroxides.

The concentration of the catalyst, formally reported in ppm (mass) of catalyst metal based on the total mass, is from 0.01 ppm to 1000 ppm, preferably from 0.5 to 100 ppm, particularly preferably from 1 to 50 ppm.

The ratio [mol/mol] of carbene to metal is from 0.01:1 to 250:1, preferably from 1:1 to 100:1, particularly preferably from 1:1 to 50:1. In addition to the carbene ligands, further ligands, for example phosphorus ligands such as triphenylphosphine, may be present in the reaction mixture.

Owing to the catalyst activities and stabilities, it is possible to use extremely small amounts of catalyst in the process of the invention. Apart from a procedure in which the catalyst is reused, there is also the option of not recycling the catalyst. Both variants have already been described in the patent literature (WO 90/13531, U.S. Pat. No. 5,254,782, U.S. Pat. No. 4,642,392).

It is often advantageous to carry out the telomerization reaction in the presence of bases. Preference is given to using basic components having a $pK_b$ of less than 7, in particular compounds selected from the group consisting of amines, alkoxides, phenoxides, alkalimetal salts and alkaline earth metal salts.

Suitable basic components are, for example, amines such as trialkylamines which may be alicyclic or/and open-chain, amides, alkali metal salts or/and alkaline earth metal salts of aliphatic or/and aromatic carboxylic acids, e.g. acetates, propionates, benzoates, or corresponding carbonates, hydrogencarbonates, alkoxides of alkali metals and/or alkaline earth metals, phosphates, hydrogenphosphates or/and hydroxides, preferably of lithium, sodium, potassium, calcium, magnesium, cesium, ammonium and phosphonium compounds. Preferred additives are hydroxides of alkali metals and alkaline earth metals and metal salts of the nucleophile of the formula (II).

In general, the basic component is used in an amount of from 0.01 mol % and 10 mol % (based on the olefin), preferably from 0.1 mol % to 5 mol % and very particularly preferably from 0.2 mol % to 1 mol %.

In the process of the invention, the ratio [mol/mol] of diene used to nucleophile used is from 1:100 to 100:1, preferably from 1:50 to 10:1, particularly preferably from 1:10 to 2:1.

The process of the invention can be carried out continuously or batchwise and is not restricted to the use of particular types of reactor. Examples of reactors in which the reaction can be carried out are stirred tank reactors, cascades of stirred vessels, flow tubes and loop reactors. Combinations of various reactors are also possible, for example a stirred tank reactor connected to a downstream flow tube.

The following examples illustrate the invention without restricting the scope of the patent application.

EXAMPLES

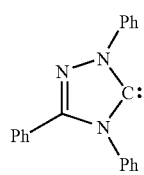

B-1

-continued

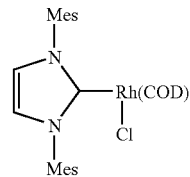

B-2

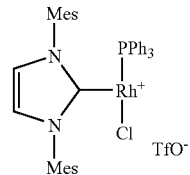

B-3

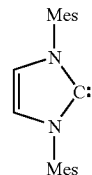

B-4

Mes=mesityl (2,4,6-trimethylphenyl); COD=1,5-cyclooctadiene; the bonding of the heterocyclic carbene ligand to the metal is, as in the technical literature, shown in the form of a single bond rather than as a double bond; TfO$^-$=trifluoromethansulfonate Example 1

Telomerization of 1,3-butadiene with methanol 211 g of degassed methanol, 589 g of 1,3-butadiene, 1.20 g of sodium hydroxide, 50 g of cyclooctane (internal GC standard) and 0.50 g of 4-t-butylcatechol were placed in a 3 liter autoclave (from Büchi) under protective gas and heated to 80° C. 0.0494 g of palladium acetylacetonate and 0.1078 g of the compound 5-methoxy-1,3,4-triphenyl-4,5-dihydro-1H-1,2,4-triazoline (from which the carbene B-1 can be formed by elimination of methanol) were separately dissolved in 48.4 g of degassed methanol under protective gas. The reaction was started by introducing the solution (from a pressure burette) into the autoclave and the course of the reaction was monitored by gas-chromatographic analysis of samples taken at regular intervals. After 180 minutes, 18% of the butadiene had reacted, and the selectivity of the reaction to 2,7-octadien-1-yl methyl ether was >96.8% according to gas-chromatographic analysis.

Example 2

Synthesis of the complex B-2: 60 mg of [Rh(COD)Cl]$_2$ (M=493.08 g/mol) are dissolved in 2 ml of THF (tetrahydrofuran) and admixed at room temperature with 76 mg of the carbene B-4 (M=304.3 g/mol) dissolved in 1 ml of THF while stirring. The solution is stirred for 3 hours, the THF is removed under reduced pressure, the precipitate is dissolved in $CH_2Cl_2$ and filtered. The $CH_2Cl_2$ is removed under reduced pressure, the residue is washed with pentane, filtered off and dried under reduced pressure. The yield is 82% (110 mg, M=550.97 g/mol).

Example 3

Synthesis of the complex B-3: 113.6 mg of B-2 (0.21 mmol, M=550.97 g/mol), dissolved in 5 ml of THF are admixed at RT with 53 mg of AgOTf (0.01 mmol, M=256.94 g/mol) and 57 mg of $PPh_3$ (0.21 mmol, M=262.28 g/mol) dissolved in 10 ml of THF. The AgCl which precipitates is filtered off and the THF is removed under reduced pressure. The residue is taken up in $CH_2Cl_2$, filtered and part of the $CH_2Cl_2$ is removed under reduced pressure. The complex is precipitated from a little $CH_2Cl_2$ by addition of pentane, filtered off, washed with pentane and dried under reduced pressure. The yield is 171.8 mg, 90% (M=926.88 g/mol).

Examples 4 and 5

General Method for the Telomerization of Butadiene with Methanol:

In a 100 ml Schlenk tube, the appropriate amount of catalyst is dissolved in 16.1 g of methanol under protective gas. The solution is admixed with 1 mol % (based on the amount of 1,3-butadiene used) of sodium methoxide (base) and 5 ml of isooctane (internal GC standard). The reaction solution is subsequently drawn into the evacuated autoclave (100 ml autoclave from Parr), the autoclave is cooled to T <−10° C. and 13.6 g of 1,3-butadiene are condensed in (amount determined by loss in mass of the butadiene stock bottle). The autoclave is warmed to the reaction temperature and then cooled to room temperature after 16 hours. Unreacted 1,3-butadiene is condensed back into a cold trap cooled by means of dry ice. The reaction mixture in the reactor is analyzed by gas chromatography.

The telomerization of 1,3-butadiene with methanol was carried out in accordance with the general method using the complexes B-2 and B-3. The reaction temperature was 90° C.

The main product obtained in the reaction was 1-methoxyocta-2,7-diene (n product). In addition, 3-methoxyocta-1,7-diene (iso product), 1,3,7-octatriene (OT), 1,7-octadiene (OD) and vinylcyclohexene (VCEN) were formed.

The invention claimed is:

1. A process for the catalytic telomerization of an acyclic olefin having at least two conjugated double bonds (I)

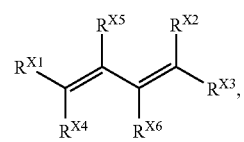

comprising:

removing alkynes and 1,2-butadiene, if present, from a mixture of 1,3-butadiene with other $C_3$-, $C_4$- and/or $C_5$-hydrocarbons; and then telomerizing said treated mixture of 1,3-butadiene with other $C_3$-, $C_4$- and/or $C_5$-hydrocarbons, as said acyclic olefin having at least two conjugated double bonds, with at least one nucleophile, and one or more complexes comprising one or more metals of groups 8 to 10 of the Periodic Table of the Elements and at least one carbene ligand having one of the following formulae

| Ex. No. | MeOH:butadiene | Cat. | Rh [Mol-%] | Base [Mol-%] | n + iso [%] | n:iso [%] | OT + OD + VCH [%] | TON |
|---|---|---|---|---|---|---|---|---|
| 4 | 1:2 | B-2 | 0.021 | 1 | 4.6 | 97.7:2.3 | 2.4 | 219 |
| 5 | 1:2 | B-3 | 0.021 | 1 | 1.1 | 95:5 | 2.7 | 52 | n + iso = Yield of n product and iso product n:iso = Ratio of n product to iso product OT + OD + VCH = Yield of 1,3,7-octatriene, 1,7-octadiene, vinylcyclohexene (total)

TON = turnover number

-continued

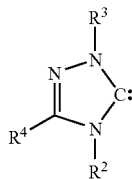
(VI)

where $R^{X1}$, $R^{X2}$, $R^{X3}$, $R^{X4}$, $R^{X5}$, $R^{X6}$: are each H $R^2$; $R^3$: are identical or different and are each a) a linear, branched, substituted or unsubstituted cyclic or alicyclic alkyl group having from 1 to 24 carbon atoms, or b) a substituted or unsubstituted, monocyclic or polycyclic aryl group having from 6 to 24 carbon atoms or c) a monocyclic or polycyclic, substituted or unsubstituted heterocycle having from 4 to 24 carbon atoms and at least one heteroatom selected from the group consisting of N, O, and S, $R^4$, $R^5$, $R^6$, $R^7$, are identical or different and are each hydrogen, alkyl, aryl, heteroaryl, —CN, —COOH, —COO-alkyl, —COO-aryl, —OCO-alkyl, —OCO-aryl, —OCOO-alkyl, —OCOO-aryl, —CHO, —CO-alkyl, —CO-aryl, —O-alkyl, —O-aryl, —NH$_2$, —NH(alkyl), —N(alkyl)$_2$, —NH(aryl), —N(alkyl)$_2$, —F, —Cl, —Br, —I, —OH, —CF$_3$, —NO$_2$, -ferrocenyl, —SO$_3$H, —PO$_3$H$_2$, where the alkyl groups have 1-24 carbon atoms and the aryl groups have from 5 to 24 carbon atoms and the radicals $R^4$ and $R^5$ optionally are part of a bridging aliphatic or aromatic ring, wherein, when the catalytically active metal of groups 8 to 10 of the Periodic Table is Pd, substituents $R^2$ and/or $R^3$ are as defined in subgroup (c) above.

2. The process as claimed in claim 1, wherein $R^2$, $R^3$, $R^4$, $R^5$, $R^6$ and $R^7$ are identical or different and have at least one substituent selected from the group consisting of —H, —CN, —COOH, —COO-alkyl, —COO-aryl, —OCO-alkyl, —OCO-aryl, —OCOO-alkyl, —OCOO-aryl, —CHO, —CO-alkyl, —CO-aryl, -aryl, -alkyl, -alkenyl, -allyl, —O-alkyl, —O-aryl, NH$_2$, —NH(alkyl), —NH(aryl), —N(alkyl)$_2$, —F, —Cl, —Br, —I, —OH, CF$_3$, —NO$_2$, -ferrocenyl, SO$_3$H, and —PO$_3$H$_2$, wherein the alkyl groups have from 1 to 24, the alkenyl groups have from 2 to 24 carbon atoms, the allyl groups have from 3 to 24 carbon atoms and the aryl groups have from 5 to 24 carbon atoms.

3. The process as claimed in claim 1, wherein said nucleophile has formula (II)

(II)

where Z is O, N(R$^{1''}$), S(O$_2$), Si(R$^{1''}$)(OH), C=O, C(H$_2$), C(H)(NO$_2$) or N(CH$_2$CH=CH$_2$) and R$^1$, R$^{1'}$ or R$^{1''}$ are identical or different and are each H, a substituted or unsubstituted, linear, branched or cyclic alkyl or alkenyl group having from 1 to 22 carbon atoms, a carboxyl group or an aryl group, where the radicals R$^1$, R$^{1'}$ may be joined to one another via covalent bonds and R$^1$ and R$^{1'}$ may bear identical or different substituents.

4. The process as claimed in claim 1, wherein said nucleophile is a compound of formula (IIa) or (IIb)

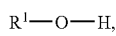
(IIa)

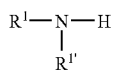
(IIb)

where R$^1$, R$^{1'}$ are identical or different and are each H, a substituted or unsubstituted, linear, branched or cyclic alkyl or alkenyl group having from 1 to 22 carbon atoms, a carboxyl group or an aryl group and the radicals R$^1$, R$^{1'}$ may be joined to one another via covalent bonds.

5. The process as claimed in claim 1, wherein said nucleophile is selected from the group consisting of water, one or more alcohols, one or more phenols, one or more polyols, one or more carboxylic acids, ammonia, one or more primary or secondary amines and combinations thereof.

6. The process as claimed in claim 1, carried out in a solvent, which is said nucleophile and/or an inert organic solvent.

7. The process as claimed in claim 1, wherein of said carbene ligand and metal are combined in a molar ratio of carbene to metal ranging from 0.01:1 to 250:1.

* * * * *